United States Patent [19]

Gressel et al.

[11] Patent Number: 4,900,676
[45] Date of Patent: Feb. 13, 1990

[54] METHOD OF PRODUCING HERBICIDE RESISTANT PLANT VARIETIES AND PLANTS PRODUCED THEREBY

[75] Inventors: Jonathan Gressel, Havazelet; Dvora Aviv, Rehovot; Avihai Perl, Rishon-Le-Zion, all of Israel

[73] Assignee: Yeda Research and Development Co. Ltd., Rehovot, Israel

[21] Appl. No.: 17,870

[22] Filed: Feb. 24, 1987

Related U.S. Application Data

[63] Continuation-in-part of Ser. No. 704,416, Feb. 22, 1985, Pat. No. 4,795,705.

[30] Foreign Application Priority Data

Feb. 23, 1986 [IL] Israel ......................................... 77962

[51] Int. Cl.[4] .............................................. C12N 5/00
[52] U.S. Cl. .......................... 435/240.49; 435/240.51; 435/240.54
[58] Field of Search ................ 435/172.2, 240.47, 173, 435/240.49, 240.5, 240.54, 240.51; 800/1; 47/58

[56] References Cited

PUBLICATIONS

Bokelmann et al., 1983, Z. Pflanzen Physiol., 109(3): 259–265.
Webb et al., 1983, Plant Science Letters, 30(1): 1–8.
Ahloowalia, B., 1982, Euphytica, 31(3): 755–759.
Miller et al., 1984, pp. 314–315, In: Handbook of Plant Cell Culture, vol. 3, (Ammirato et al., eds.), MacMillen: New York.

*Primary Examiner*—Charles F. Warren
*Assistant Examiner*—David T. Fox
*Attorney, Agent, or Firm*—John P. White

[57] ABSTRACT

A method of introducing cytoplasmically inherited traits from a donor plant into a receptor plant of the Solanaceae family has been invented. A method is provided for producing *Solanum tuberosum* plants which have the inherited trait. Protoplasts from the donor and receptor plants are prepared. The donor protoplasts are treated under suitable conditions to prevent extensive nuclear divisions. The treated donor protoplasts and receptor protoplasts are then contacted under suitable conditions permitting the fusion of the protoplasts. Plantlets are regenerated from the fused protoplasts, and plantlets which contain the donor cytoplasmic traits are selected and rooted. Plantlets which contain recpetor cytoplasmic traits are discarded.

10 Claims, No Drawings

METHOD OF PRODUCING HERBICIDE RESISTANT PLANT VARIETIES AND PLANTS PRODUCED THEREBY

BACKGROUND OF THE INVENTION

This application is a continuation-in-part of U.S. Ser. No. 704,416, filed Feb. 22, 1985, U.S. Pat. No. 4,795,705, the contents of which is hereby incorporated by reference.

Throughout this application various publications are referenced by the names of the authors and the year of publication within parentheses. Full citations for these publications may be found at the end of the specification immediately preceding the claims. The disclosures of these publications in their entireties are hereby incorporated by reference into this application in order to more fully describe the state of the art to which this invention pertains.

This invention relates to the rapid development of plant varieties resistant to certain types of costeffective herbicides. It includes the production of new crop varieties resistant to such herbicides including potatos and certain Solanaceous crops, as well as other crops produced asexually or through seeds. The invention is limited only by the compatibility of the cytoplasms from a resistant species with the nucleus and other cellular components of the crop in question.

Certain weed species that were under intensive selection pressure in the field, have evolved resistance to the chloro-s-triazine group of herbicides (cf. LeBaron and Gressel, 1982). This resistance could be useful in areas where this group of herbicides has not been overused, and with crops that need a good broad-spectrum herbicide with sufficient soil residual activity as to give season long control of weeds in that crop. Genetic experiments have shown that this triazine resistance in weeds is often maternally inherited (cf. Souza-Machado, 1982), and biochemical evidence suggests that this trait is inherited in such cases on the DNA of the chloroplasts. Thus, it is necessary to transfer only chloroplasts to a crop in order to confer resistance. The first case of possible maternal inheritance of triazine resistance was found in *Brassica campestris* (cf. Souza-Machado, 1982). Just after this was found, it was suggested that this trait be somehow transferred to the crop *Brassica napus* (rape seed) using the new procedures of protoplast fusion (Gressel et al, 1978). Despite this suggestion, scientists transferred triazine resistance by crossing the two species, and backcrossing to *B. napus* until a new variety was ready (cf. Souza-Machado, 1982), a process requiring more than 5 years of crosses and back-crosses. The methodology of cybridization (transferring of only cytoplasmic genomes without the nuclear genome, by protoplast fusion) had only been worked out in sufficient detail for Nicotiana (Zelcer et al, 1978) and in a few other cases Real successes with this methodology was not achieved with crops, even though there are many resistant-weed; susceptible-crop pairs with sufficient relatedness to expect that such a transfer could be successfully accomplished (Gressel et al, 1982). Indeed, previous attempts using the methods of Zelcer et al. (1978) were only able to perform fusions which contained the nuclei of triazine-resistant *Solanum nigrum* (Black Nightshade) as well as nuclei *S. tuberosum* (potato). The fusion products segregated, as expected to plantlets which are triazine resistant and plantlets which were susceptible to triazine. (Binding et al, 1983). Of the more then 2000 plants tested, only one resembled *S. Nigrum*; but it was triazine susceptible and contained chloroplasts which were biochemically determined to be those of potato (Gressel et al, 1982). This showed that spontaneous cybridizations could occur, but this would not be a practical method. This also showed compatibility between nightshade nuclei and potato chloroplasts, although the reverse need not have necessarily been so.

The methods of this invention can also be used to transfer maternally inherited resistance to other herbicides. (cf. Gressel, 1985). Such resistance would be easier to transfer from variety to variety by means of directed protoplast fusion of this invention. Other cytoplasmically inherited traits can be transferred using the same methodologies.

SUMMARY OF THE INVENTION

A method of introducing cytoplasmically inherited traits from a donor plant, e.g. herbicide resistance, into a receptor plant of the Solanacae family such as a potato or tomato has been invented.

According to the invention protoplasts from the donor and receptor plant are prepared. The donor protoplasts are then treated under suitable conditions to prevent extensive nuclear divisions. This treatment may be a chemical treatment, but it is preferably a treatment with X-ray irradiation.

The treated donor protoplasts and receptor protoplasts are then contacted under suitable conditions permitting fusion of the protoplasts. Plantlets are then regenerated from the fused protoplasts.

The plantlets which contain donor cytoplasmic traits are selected and rooted. Plantlets which contain receptor cytoplasmic traits are discarded.

One embodiment of the invention concerns the transfer of cytoplasmically inherited resistance to the herbicide atrazine from *Solanum nigrum* to the potato *Solanum tuberosum* cv. Mirka. In this embodiment the *Solanum nigrum* protoplasts are treated with X-ray radiation before fusing them with the *Solanum tuberosum* protoplasts. The X-ray dose is in an amount greater than the X-ray dosage necessary to prevent the *Solanum nigrum* protoplast from regenerating by itself. e.g. 7,000 rads. Using this method fused protoplasts are obtained which have *Solanum tuberosum* nuclear along with *Solanum nigrum* cytoplasmic traits, e.g. atrazine resistance.

The invention also concerns protoplasts, plants and stem explants derived from these plantlets such as the atrazine resistant stem explant of *Solanum tuberosum* cv. Mirka Tri-R C-165, ATCC Accession No. 40164, or *Solanum tuberosum* cv. Desiree Tri-R, ATCC Accession No. 40224.

A method of introducing the cytoplasmically inherited trait of triazine resistance from *Solanum nigrum* into *Solanum tuberosum* cv. Desiree comprises:

(a) preparing protoplasts from the *Solanum nigrum* and *Solanum tuberosum* cv. Desiree;

(b) treating the protoplasts derived from *Solanum nigrum* with a suitable dose of X-ray irradiation under suitable conditions, a dose being greater than the dose needed to prevent the *Solanum nigrum* protoplasts from regenerating by themselves;

(c) contacting the treated *Solanum nigrum* protoplasts with the *Solanum tuberosum* cv. Desiree protoplasts under suitable conditions permitting fusion of the protoplasts;

(d) regenerating the fused protoplasts so as to form plantlets; and (e) selecting and rooting the *Solanum tuberosum* cv. Desiree plantlets with triazine resistant traits.

A method of producing *Solanum tuberosum* cv. Mirka plants comprises:

(a) vegetatively propagating stem explants or calli of meristem shoots of *Solanum tuberosum* cv. Mirka Tri-R C-165 (ATCC Accession No. 40164) in a suitable first growth medium and under suitable conditions to generate plantlets having shoots and roots; and (b) transferring the plantlets having a sufficient root system to a suitable second growth medium, wherein the rooted plantlets are propagated under suitable conditions to produce mature *Solanum tuberosum* cv. Mirka plants.

A method of producing *Solanum tuberosum* cv. Desiree plants comprises:

(a) vegetatively propagating stem explants or calli of stem explants of *Solanum tuberosum* cv. Desiree Tri-R (ATCC Accession No. 40224) in a suitable first growth medium and under suitable conditions to generate plantlets having shoots and roots; and (b) transferring the plantlets having a sufficient root system to a suitable second growth medium, wherein the rooted plantlets are propagated under suitable conditions to produce mature *Solanum tuberosum* cv. Desiree plants.

DETAILED DESCRIPTION OF THE INVENTION

The present invention concerns a method of introducing cytoplasmically inherited traits from a donor plant into a receptor plant of the Solanacea family, such as a potato, tomato, eggplant or pepper. The cytoplasmically inherited trait can be any useful trait such as a resistance to a specific herbicide, e.g. a triazine herbicide. The donor and receptor plants can be plants of different species or different varieties of plants within a species. In a specific embodiment of the invention the cytoplasmically inherited trait of triazine resistance of the black nightshade *Solanum nigrum* is transfered to the potato *Solanum tuberosum*. The methods of the invention may also be used for instance to transfer the cytoplasmically inherited trait from a donor triazine resistant potato to a tomato.

According to the methods of the invention protoplasts are prepared from the donor and receptor plants. The donor protoplasts are then treated under suitable conditions so as to prevent extensive nuclear divisions of the donor protoplasts. This treatment can be by chemical means or any other means. The treatment is preferably a treatment with a dose of X-ray radiation. A suitable dose of X-ray radiation is a dose which is greater than the dose needed to prevent a donor protoplast from regenerating by itself.

The treated donor protoplasts and the receptor protoplasts are contacted under suitable conditions permitting the fusion of the protoplasts. The fused protoplasts are then regenerated to form plantlets. The plantlets which exhibit and contain donor cytoplasmic traits, e.g. herbicide resistance, are selected and rooted. Those plantlets which contain receptor cytoplasmic traits are discarded. Stem explants of these plantlets may also be prepared.

The invention also concerns the fused protoplasts, plantlets and stem explants prepared by the methods of this invention.

A specific embodiment of the invention involves introducing a cytoplasmically inherited resistance to a triazine herbicide, e.g. atrazine from *Solanum nigrum* into the potato *Solanum tuberosum* cv. Mirka.

Another specific embodiment of the invention involves introducing a cytoplasmically inherited resistance to a triazine herbicide, e.g. atrazine from *Solanum nigrum* into the potato *Solanum tuberosum* cv. Desiree.

Protoplasts from the *S. Nigrum* and *S. tuberosum* are prepared. The protoplasts derived from the *S. nigrum* are treated with a suitable dose of X-rays under suitable conditions in order to inactivate the *S. nigrum* nuclei. A suitable dose of X-rays is a dose greater than the dose needed to prevent an *S. nigrum* protoplast from regenerating by itself, e.g. 7,000 rads.

The treated *S. nigrum* protoplasts are then contacted with the *S. tuberosum* protoplasts under suitable conditions permitting fusion of the protoplasts. The fused protoplasts are regenerated to form plantlets. Plantlets which are atrazine resistant and contain the cytoplasmically inherited trait are selected and rooted. Stem explants can also be prepared from these plantlets.

A stem explant of the atrazine resistant derivative of *Solanum tuberosum* cv. Mirka produced by the methods of this invention and designated as strain C-165, has been deposited as meristem shoots with the American Type Culture Collection, 12301 Parklawn Drive, Rockville, Maryland 20852 and has been assigned Accession No. 40164.

A method of introducing the cytoplasmically inherited trait of triazine resistance from *Solanum nigrum* into *Solanum tuberosum* cv. Desiree comprises:

(a) preparing protoplasts from the *Solanum nigrum* and *Solanum tuberosum* cv. Desiree;

(b) treating the protoplasts derived from *Solanum nigrum* with a suitable dose of X-ray irradiation under suitable conditions, a dose being greater than the dose needed to prevent the *Solanum nigrum* protoplasts from regenerating by themselves;

(c) contacting the treated *Solanum nigrum* protoplasts with the *Solanum tuberosum* cv. Desiree protoplasts under suitable conditions permitting fusion of the protoplasts;

(d) regenerating the fused protoplasts so as to form plantlets; and (e) selecting and rooting the *Solanum tuberosum* cv. Desiree plantlets with triazine resistant traits.

A method of producing *Solanum tuberosum* cv. Mirka plants comprises:

(a) vegetatively propagating stem explants or calli of meristem shoots of *Solanum tuberosum* cv. Mirka Tri-R C-165 (ATCC Accession No. 40164) in a suitable first growth medium and under suitable conditions to generate plantlets having shoots and roots; and (b) transferring the plantlets having a sufficient root system to a suitable second growth medium, wherein the rooted plantlets are propagated under suitable conditions to produce mature *Solanum tuberosum* cv. Mirka plants.

The conditions for generating roots may comprise transferring the shoots to a suitable medium which induces rooting. The first growth medium may be an agar or agarose nutrient medium, which may also contain a plant growth hormone. The first growth medium may be the modified Murashige and Skoog basal medium of Table 1 to which has been added gibberellic acid, abscissic acid, zeatin (trans-isomer) and kinetin. The conditions for generating shoots may comprise light and a temperature of about 24° C. The second growth medium may be soil.

A method of producing *Solanum tuberosum* cv. Desiree plants comprises:

(a) vegetatively propagating stem explants or calli of stem explants of *Solanum tuberosum* cv. Desiree Tri-R (ATCC Accession No. 40224) in a suitable first growth medium and under suitable conditions to generate plantlets having shoots and roots; and (b) transferring the plantlets having a sufficient root system to a suitable second growth medium, wherein the rooted plantlets are propagated under suitable conditions to produce mature *Solanum tuberosum* cv. Desiree plants.

The conditions for generating roots may comprise transfering the shoots to a suitable medium which induces rooting. The first growth medium may be an agar or agarose nutrient medium, which may also contain a plant growth hormone. The first growth medium may be the modified Murashige and Skoog basal medium of Table 1 to which has been added gibberellic acid, naphthalene acetic acid, zeatin (trans-isomer) and zeatin riboside. The conditions for generating shoots may comprise light and a temperature of about 24° C. The second growth medium may be soil.

DEVELOPMENT OF CYBRIDIZATION STRATEGY

As an initial step in the development and production of new varieties to carry exogenous cytoplasmic genes, a strategy is formulated. Broadly stated, donor plants are chosen with an appropriate and desirable genetic trait needed in a recipient species. The particular desirable traits are, defined by the commercial requirements of the market (e.g. cytoplasmically inherited herbicide, disease toxin, or antibiotic resistances, cytoplasmic male sterility or other cytoplasmically inherited traits), and the farming practice to be used. A specific embodiment of the invention concerns the transfer of triazine resistance by cybridization.

Heretofore, many of these traits could not be transferred by normal genetic means, e.g. pollination because the desirable donor and the recipient were not sufficiently related. Even when they are related, the number of crosses and back-crosses requires years of work. According to this invention, the breeder can now quickly transfer genetic information between donor and recipient without the need of multiple backcrosses. The procedure is limited only by the cytoplasmic-nuclear compatibilities between donor and recipient. Accordingly, the strategy may take advantage of any desirable trait found in any single plant as long as it is cytoplasmically inherited and there is compatibility between the donor and the recipient.

Once triazine resistance is transferred from a weed to a crop variety, it may be easier to transfer this trait by specific fusion procedures from one variety to the next than by transfer from the weed itself to the second variety.

Stated differently, the breeder is no longer limited to crosses within a species. There is the possibility of utilizing cytoplasmically inherited traits in related species, although how closely related they must be is not clear. The system precludes the need of backcrossing.

Moreover, the large number of cybrid fusants that can be regenerated into plants in a single experiment permits optimum selection of true to type varietal derivatives (new varieties differing from the parent variety only in the new trait), from among possible somaclonal variants. Conversely, it allows screening for superior somaclonal variants bearing the transferred cytoplasmic trait.

SELECTION OF INDIVIDUAL PARENT PLANTS

The donor: In the case of triazine-resistance, there has been concurrent evolution to resistance, separately, in various locales. As there is a genetic cost to all mutations leading to evolution, it is best to try to first measure this cost, and to choose the most fit line for cybridizations. The preferred method of testing for fitness for cybridization is a method using a mixed culture of the plants from various lines bearing the traits. This is preferably done with $F_1$ reciprocal hybrids of the two lines being compared, to give them the same hybrid nuclei, and the separate cytoplasms. Cytoplasmic fitness can also be measured while cybridizations are done. As other characteristics, which may or may not be found in the ultimate cybrid plants may affect fitness, a few good lines must be used. Fitness should again be checked on the cybrids.

It must be ascertained that the trait in question is cytoplasmically inherited. Triazine resistance in maize and in some of the algae is inherited on the nuclear genome. In most weeds and other algae this trait is maternally inherited.

The donor plants should be checked for freedom of disease infestation.

In a preferred embodiment, a population of 3-10 plants of each of the 3-5 better biotypes are chosen as donor plants.

The recipient: The recipient plant can be any name variety or breeders breeding material, to which one wishes to insert the given trait. In the case of vegetatively propagated material such as potatos, good varietal material should be used. In the case of crops which are $F_1$ hybrids or other hybrids, the recipient must be the female line used in generating such hybrids, as the traits embodied in this invention are all inherited on the female line only.

The material should usually be disease and virus free, unless some viral or viral like inherited trait is desirable.

Obtaining clonable explant material for preparing protoplasts

Disease and pest free protoplasts can be best obtained from explant material growing under controlled environmental conditions. After designation of the individual parent plants, suitable primary explant tissue must be obtained. The explant is basically a vegetatively propagated cloned material of the parents, grown axenically utilizing tissue culture techniques.

Primary explants or seedlings

Obtaining the primary explant tissue depends largely upon the particular species in question. In highly homozygous, normally self-pollinated species such as many of the Solanaceae, it is simplest to surface sterilize seeds and germinate them on a sterile, agar-gel mineral medium. In the case of more heterozygous material one must surface sterilize plumules or axillary buds with pieces of stem tissue. In the case of potatos, surface sterilized buds are excised from scrubbed tubers or stem pieces growing out of a "germinated" (sprouted) tuber.

All treatments following the initial surface washing in detergent, surface sterilization with either hypochlorite, 70% ethanol in water, or mercuric chloride, singly or in sequence, are performed under axenic conditions. Sterile scalpels, forceps and other equipment are used for the actual excision and for transfer of explant tissue.

It is desirable that several explants are taken from each plant to ensure the availability of sufficient material and to balance the small amount of microbial contamination and mortality which occur in tissue culture procedures.

Aseptic laboratory conditions are maintained for further cloning the explants on sterile mineral medium, with or without addition of various organic nutrients or growth factors.

Propagational cloning of explant material

The parental seedlings or explants are further vegetatively propagated to obtain sufficient amounts of genetically similar leaf tissue for obtaining protoplasts. The primary explants or seedlings are allowed to grow until they develop a few internodes on a mineral water, agar gelled medium as above. The media compositions contain a balance of inorganic ions needed for plant growth. Often sucrose or other sugars are added as a carbon source, although in some cases it is desirable to use lights as the sole energy source, via photosynthetic carbon fixation Explant material usually does not require any nitrogen source more complex than ammonium or nitrate ions, but aminoacids can be added. Vitamins and hormones need not necessarily be supplied, unless a rooting hormone, e.g. auxin, is desired. Such nutrient media are described in many standard references and are known to those of ordinary skill in the art. The nutrient, light and gas balance optimal for growing explants to obtain regenerable protoplasts from the leaves can vary from species to species. The stem explant pieces should be perpendicular to the medium and supported by the medium. Agar or agarose are the most common gelling agents.

Such explants are usually grown in sterilized plastic or glass vessels, 3-15 cm deep and with a lid like a petri plate which allows the free diffusion of air but prevents contamination by microorganisms.

Usually the apical 1-2 cm pieces are sterily excised from the primary explants, just above a bud, and planted in the same mineral medium at fortnightly to monthly intervals. Regrowth on the primary and secondary explants is similarly excised until sufficient plantlets with leaves are available for producing protoplasts.

Depending on the particular species and often on the particular variety, different in vitro techniques have been found desirable to quickly generate enough axenic plantlets to begin preparing protoplasts. At times, when very small pieces such as single tiny buds are used, it may be necessary to add hormones and vitamins.

Preparation of Protoplasts

Protoplasts are usually and preferably prepared from axenically grown, uniform leaf tissue, which is infiltrated with a sterile mixture of cellulases and pectinases in a high osmoticum medium. The infiltration can be performed by cutting the leaves into thin strips which are floated on this medium, by peeling off the epidermis with its hydrophobic cuticle or piercing the tissue with pin size holes. The high osmoticum is usually obtained by using non-metabolized or poorly metabolized sugars or sugar alcohols such as mannitol or sorbitol. The effect of the osmoticum is to partially plasmolyze and thus separate the protoplast from the cell wall, and to prevent the protoplast from bursting when the cell wall is removed. The cellulases and pectinases remove the cell wall material, releasing protoplasts into the medium. Because of the high organic content of the media, the multiple manipulations, and the possibility of a minor contamination of explant leaves, it is common to add various antibiotics to the media. These will control minor infestations but can not control massive ones.

The elucidation of the optimal mixture of enzymes, the best conditions of infiltration, the concentration of the osmoticum and the mineral medium, the temperature and duration of incubation, the light regime, whether shaking is used, etc. vary from species to species and to some extent, between varieties. The best conditions for obtaining viable and regenerable protoplasts must be determined, mainly empirically, for each case. Many procedures have been published which do work in the laboratory from which they emanated, but are not as good, for unknown reasons, in other laboratories.

Inactivation of donor nuclei

Various techniques can be used to prevent the nuclei of donor protoplasts from contributing to the fusant plants. We prefer a highly controllable technique involving X-rays. Unlike chemical treatments, the dose is given while the machine is on, and stopped once it is turned off. Another disadvantage in using chemicals is that some chemicals do not freely diffuse out of protoplasts. The X-ray treatment, can be given to protoplasts themselves or directly to the leaf tissue while it is being incubated with the enzymes, near the end of the incubation period. The donor protoplasts must be washed free of possible toxic products produced by ionization off the medium during X-ray irradiation.

It had previously been found with Nicotiana fusions that if the X-ray dosage is sufficient to preclude division of donor protoplasts, then donor nuclear characters will not be found in fusants. We found that this is not so with *Solanum nigrum*. A dose was given after which no protoplasts divided in the *S. nigrum* controls but still gave fusants with many *S. nigrum* properties upon regeneration. This suggested that unaffected *S. nigrum* chromosomes could exist in the fusant with its one non-irradiated set of recipient nuclear chromosomes. Such unaffected chromosomes could not exist in *S. nigrum* nuclei as one or a few X-ray "hits" are sufficient to prevent subsequent divisions. It is thus necessary to treat donor protoplasts with much higher doses than needed when they are to be regenerated when alone. There is evidence that nuclei thus treated are actually active and can produce metabolic products, e.g messenger RNA, necessary for the viability of the fusant and the first divisions. Such nuclei may even undergo a division or two before the defects induced by the treatments prevent further divisions. This may be an advantage over physical removal of the nuclei by centrifugation or micro-injection of the plastids.

Other methods of donor nucleus inactivation may also be used, e.g chemical inactivation with aphidicolin or hydroxyurea.

Protoplast fusion

The protoplasts from the donor (with nuclei treated to prevent long-term nuclear viability), and the protoplasts from the recipient are separately washed and then mixed together at critical cell densities. Fusion of the protoplasts can be induced by transiently increasing the pH, the divalent cation concentrations (particularly calcium) or by adding polyethylene glycol; either separately or as a mixtures of two or three of the above methods. The critical cell densities, the optimal concentrations of divalent cations, the optimal pH, the optimum polyethylene glycol concentration and average molecular mass, the optimal temperature, the optimal duration of incubation, and the optimal osmoticum are all factors which vary from species to species and variety to variety. These optima are determined for each pair of donor and recipient.

To preclude too much self-fusion of the recipient and to preclude non-fused recipient protoplasts from becoming the predominant product regenerating following the treatment to induce fusion, a few strategies are employed. Conditions can be used whereby a metabolic product under the control of the treated donor nucleus is needed for the first division of the fusant. This strategy was successfully followed for Nicotiana interspecific cybridization (Zelcer et al., 1978). Another strategy is to use a high ratio of donor protoplasts to recipients to decrease the probability of recipient self-fusions and to increase the possibility of the recipient fusing with more than one donor protoplast.

Following the incubation period with the factor or factors promoting fusion, the fusion promoting factors are quickly washed out, to prevent permanent membrane damage, with a series of high-osmoticum buffers.

Sometimes the fusants are "hardened" by culturing for a period in a medium which allows better regeneration of a cell wall but precludes division. The mineral, metabolizable sugar, and the inorganic and organic forms of nitrogen and growth factor compositions in the division medium are rather critical and species and variety specific, as are light and temperature conditions.

As cells begin division into microcolonies, the osmoticum is lowered by changing the media at intervals.

Eventually, healthy micro-colonies are picked and transferred to an agar gelled medium with a specific mineral nutrient organic and hormone composition for each situation and calli are allowed to develop.

The state of the art of protoplast fusion and regeneration to calli and plants is intensively reviewed in Galun, E. and Aviv, D. (1983) Cytoplasmic Hybridization, Genetic and Breeding Applications, Handbook of Plant Cell Culture, Vol. 1, Editors, Evans, D. A., Sharp W. A. Amirato, P. V. Yamada, Y.

Regeneration of plantlets

Shoots can be regenerated in a single or multistep process. The micro-calli can be transferred to a medium which will induce them to commence shoot formation as well as continue to produce certain amounts of undifferentiated callus. Conversely, the micro-calli can be transferred to a medium which will support and induce only undifferentiated growth. Such calli grow rapidly and can be continually transferred to the same medium, or pieces can be transferred to a medium with a hormone balance that will induce shoot formation. There should be far less somaclonal variation with the first method. The first method usually yields shoots for testing faster than the second method.

Protoplasts which regenerate back to dividing cells can, in some cases, be placed on media which will induce them to develop into embryoids which can then be (pseudo) germinated to provide seedlings. These seedlings can be cultured as clones by cutting them as outlined in the section on propagating the primary explants.

Regenerated plantlets are also carefully observed for marker morphological characteristics so that plantlets with donor nuclear traits can be rogued.

Initial Selection of Desirable Regenerants

After fusion and cell division of the fusants, the plants derived from any given regenerated micro-callus usually bear the plastids or mitochondria of either the donor or the recipient. Sometimes this segregation of cytoplasmic genomes to one type or the other occurs only at the level of the individual shoot, and different shoots arising from a given callus can have either parental type. It is thus necessary to screen the shoots that derive directly from the callus. The preferred embodiment is to establish a shoot culture of each shoot separately, and when explants can be removed from that shoot, screening is performed on that explant.

The explant medium is prepared with the selector incorporated into it at a concentration which is nonlethal to the donor plant and lethal to the recipient (prior to introduction of donor cytoplasmic genomes). In the example cited below, atrazine was added to the medium as a selector. Those plants still bearing the recipient traits will become severely inhibited or die, and those with the donor traits remain viable.

There may be cases where the selector does not act through a cut stem i.e. where it must be applied to roots or conversely where it must be applied directly to leaf tissue. There are also possibilities that medium components such as sugars, organic or inorganic nitrogen sources, or growth regulators could counteract the effect of the selector. Such possibilities must be taken into consideration and protocols under all the above circumstances must be modified accordingly.

Shoots screened and found to have the desired traits are transferred to a mineral medium with a different hormone composition to induce rooting. Following rooting, plants can be transferred to pots, sometimes with steps designed to "harden" them to the "environmental impact" of leaving highly-controlled sterile conditions, with high humidity and optimal mineral nutrition. Such potted plants can be greenhouse or field grown.

Verification by Further Trials

Plants derived from a fusant must have an acceptably uniform phenotype and similarity to the parent variety or inbred to be of significant commercial interest. It also must have a yield, at least close to the yield potential and quality of the parent, for the new trait to be cost-beneficial. The trait in question must be stable through meiosis in the case of seed propagated crops, or through long term vegetative propagation.

When the procedure of the present invention is followed, most of the plants that have passed the initial screen should stably bear the cytoplasmically inherited trait. A small proportion may still have the mixed cytoplasm of the fusant, and segregation will occur in plants regenerated from fusant calli. In our experience, stability is soon obtained, even in such mosaics. The easiest procedure is to grow up sufficient numbers of plants from each screened calli-clone (4-10) so that semiclonal variants, i.e. variants containing nuclear traits and any other variants not true to the derived form, can often be discarded. Regenerated plants can be kept under constant selection by the selector so that segregants or mosaics containing the undesirable recipient cytoplasmic traits can also be removed. In practice, after uniformity, and stability through propagation have been established, it is desirable to verify them by field trials, which are also necessary to determine yield and to determine if the donor cytoplasm has conferred undesirable as well as the desirable trait characteristics on the fusants.

Field trials (pilot production) are conducted on a semi-commercial scale to verify that the desired trait was conferred, that the variety or line is true to form, and that yields are normal. The advantage of the culture techniques is that a large number of clonal plants can quickly be produced for such trials.

At the field trial level, performance of selected fusion calli-clones, derived from experiments using different donor strains and different recipient lines of the same variety or inbred, can be monitored, and any problems can be detected before full scale commercial production and testing begins. If problems are sufficiently serious with any lines used, the calli clones can be discarded, possibly the parent clones as well, if they are defective when fused to various lines.

Commercial Production

Once fusant derived new varieties have been grown to maturity and harvested to provide pre-commercial verification in the field trials, full scale commercial production of propagules, e.g. seeds, tubers, etc., can begin. Both the material from the field tests and the calli-clones in the laboratory can be used to rapidly obtain sufficient plant material for such a scale-up.

Applications

The technique of the present invention is applicable to transferring a wide variety of desirable cytoplasmically inherited traits. The only limitation seems to be interspecific compatibilities, between cytoplasm and nuclear genomes in such cases. The extent of such compatabilities and incompatabilities is presently being studied in many laboratories. Such known characteristics worthy of transfer are resistance to certain herbicides which inhibit photosynthesis, e.g. the triazine, phenylurea and uracil groupings and possibly many others as well. Other characteristics include resistance to the toxic principles of some phytopathogenic fungi and traits such as cytoplasmic male sterility.

In the case of herbicide resistance; vegetable crops and many field crops are particularly valuable candidates for use in this invention. Triazine herbicides such as atrazine are among the least expensive on the market, provide a broad spectrum of weed control, and have sufficient residual activity to provide control throughout the season with a single preemergence application. Potatos and Solanaceous crops are especially good candidates as they need cheaper cost effective weed control. Herbicides are not developed by the chemical industry especially for the small market of such crops. The legal licensing for the "new use" of a well established herbicide such as atrazine is also simple; mainly residue studies are needed.

As triazine resistance in weeds becomes a greater problem, maternally-inherited resistance to other herbicides which kill the newly-evolved triazine resistant weeds can be transferred in an intervarietal manner. It is sufficient to obtain such resistance in one variety and it can be transferred to others by the methods of this invention.

In substance, therefore, the methods of the invention provide methods of rapidly developing and commercially producing new, commercially useful plant varieties and inbreds containing important desirable cytoplasmically inherited traits. The methods comprise steps of (a) obtaining clones of donors with the trait and recipients needful of said trait (b) obtaining protoplasts from donor and recipient (c) causing the nuclear genome of the donor to not be inherited in the final product (d) fusing the donor and recipient protoplasts, regenerating them to calli and plantlets or other types of propagules (e) screening the resulting plantlets for trueness to form of the recipient and for the presence and genetic stability of the desired trait which was transferred, and propagating and testing the resultant material.

EXAMPLE 1

Obtaining Triazine Resistance in *S. tuberosum* cv. Mirka

In this example, the maternally-inherited triazine resistance trait which evolved in the weed *Solanum nigrum* (among other weed species) was transferred into the crop *Solanum tuberosum* cv. Mirka by protoplast fusion, after treatment of the *S. nigrum* by higher X-ray doses than those needed to prevent *S. nigrum* from regenerating by itself.

Preparation of initial explants (a) Donor—*Solanum nigrum*

*Solanum nigrum* seeds of a biotype that evolved resistance in France were provided by Dr. Jacques Gasquez, INRA, Dijon, France. Plants from these seeds were grown to adulthood, and checked for atrazine resistance. Ripe fruit from atrazine resistant plants were collected, and seeds were removed by squeezing the fruit in water. The debris was washed away with distilled water and the seeds were air dried. Dry seeds were put in 2% potassium nitrate for 10 minutes, washed one time with distilled water, and then incubated in a 50 mg/l of a gibberellic acid (Sigma Biochemicals) solution in water for 15 minutes. After incubation the seeds were washed with distilled water. The seeds, after this pretreatment which stimulates uniform germination, were surface sterilized with 1.5% of a commercial sodium hypochlorite solution for 20 minutes and then washed 5 times in sterile distilled water. All treatments were performed in a 3 ml hypodermic syringe, at room temperature.

The seeds were planted in polycarbonate sterile culture containers of a diameter of 8.5 cm and—a height of 11 cm, containing 50 ml Murashige and Skoog Basal Medium (Table I).

TABLE 1

| Modified Murashige and Skoog (1962) Basal Medium | | | |
|---|---|---|---|
| Major elements | mg/l | Organic additives | mg/l |
| $NH_4NO_3$ | 1650 | glycine | 2 |
| $KNO_3$ | 1900 | meso-inositol | 100 |
| $CaCl_2.2H_2O$ | 440 | thiamine HCl | 10 |
| $MgSO_4.7H_2O$ | 370 | nicotinic acid | 0.5 |
| $KH_2PO_4$ | 170 | pyridoxine | 0.5 |
| FeEDTA | 35 | Biotin | 0.5 |

TABLE 1-continued
Modified Murashige and Skoog (1962) Basal Medium

| | | folic acid | 0.5 |
|---|---|---|---|
| Microelements | | | |
| $H_3BO_3$ | 6.2 | | |
| $MnSO_4$ | 22.3 | | |
| $ZnSO_4.4H_2O$ | 8.6 | casein hydrolysate | 800 |
| KI | 0.83 | sucrose 30 g/l* | |
| $Na_2MoO_4.2H_2O$ | 0.25 | agar 10 g/l* | |
| $CuSO_4.5H_2O$ | 0.25 | | |
| $CoSO_4.7H_2O$ | 0.03 | | | pH brought to 5.8 with NaOH prior to autoclaving.
*unless otherwise noted

The medium was gelled with 1% Bacto-Agar (Difco). Germination and growth were at 25° C. under cool-white fluorescent lighting giving 6000–7000 lux. Twenty to twenty-five seeds were planted in each dish. More than 90% germination occurred within 5 days. Dishes were thinned so as to contain 5 healthy, rapidly growing seedlings each. The leaves were used directly for obtaining protoplasts. Every 3–4 weeks, the upper half of each plant was excised with or without the leaves and transplanted to fresh medium. The leaves are used for protoplast preparation.

(b) Recipient.—*Solanum tuberosum* cv. Mirka

Healthy tubers of *Solanum tuberosum* cv. Mirka were grown in the green house. After many shoots were well developed, ca.4 cm lengths of stem containing one axillary bud with leaf and petiole were removed and washed in running tap water for 5 minutes After washing the stems were placed in 70% ethanol for 10 seconds, transferred to 1.5% commercial sodium hypochlorite solution for 20 minutes and washed 5 times in sterile distilled water. The ends of the explant were removed and the stems with the bud facing up were placed in M & S medium (Table 1) containing 1% sucrose, and 0.8% agar. After buds were elongated to a length of 15–20 mm, they were sterily excised and transplanted to fresh dishes containing the same medium.

Explants were grown on the same M & S basal medium as the donor (Table 1) but with only 1% sucrose and 0.8% agar. Explants were transferred in the same manner as for the donor every 3–4 weeks.

Preparation of protoplasts (a) Two grams of 4 week old leaves of triazine resistant *S. nigrum* grown as explants (see previous section) were excised, and pricked with a pre-sterilized instrument bearing 70 sharp straight pins at 1 mm intervals, in such a manner that the pins totally penetrated through the leaves. This facilitates penetration of enzymes to the leaves The leaves were placed in 10 ml of an autoclaved modified N and M medium (Table 2).

TABLE 2
Modified N & M medium

| Compound | mg/l |
|---|---|
| $NaH_2PO_4.H_2O$ | 150 |
| $CaCl_2.2H_2O$ | 150 |
| $KNO_3$ | 2,500 |
| $(NH_4)_2 SO_4$ | 134 |
| $MgSO_4.7H_2O$ | 250 |
| $CaCl_2.2H_2O$ | 750 |
| $NH_4NO_3$ | 250 |
| sucrose | 153,900 (0.45 m) | pH adjusted to 5.6 with NaOH
modified from Nagy and Maliga (1976)

The medium also contains final concentrations of the following enzymes: 0.25% Cellulase "Onozuka-R-10 and 0.05% Macerozyme R-10 (both from Kinki-Yakult, Nishinomiya-Japan) and 0.125% Driselase (Kyowa Hakko Kogyo Co, Ltd, Tokyo, Japan). The enzymes were presterilized by vacuum filtration, one time, through a 0.22 micrometer pore Nalgene sterile filtration apparatus. Similarly filter sterilized ampicillin sodium salt and Kasugamycin hemi-sulfate were added to give final concentrations of 1 mg/l each. Leaf tissue and enzymes were incubated in 9 cm diameter sterile plastic petri dishes specially coated for tissue culture (Mediplast Ein Shemer, Israel, -type TC for 16 h in the dark at 24° C.

(b) Triazine sensitive *Solanum tuberosum* cv. Mirka

One group of 3 week old leaves from axenically cultivated explants was pricked as in section a, and incubated on 10 ml of a modified N & M medium (Table 2) to which were added the following enzymes (final concentrations): 0.05% Pectolyase—Y-23 (Seishin Pharmaceutical Co, Tokyo, Japan) 0.1% Driselase (Kyowa Hakko Hogyo Co. Ltd. Tokyo, Japan) 1% Meicellase (Meiji Seika Kaisha Ltd. Tokyo, Japan). These enzymes were filter sterilized as above. The same antibiotic mixture was used as in Section a. Incubation was for 16 hours, at 24° C. in the dark. (NOTE: Other varieties of potatos, and other species have other optimal enzyme mixes, incubation times etc).

Irradiation of donor

In preliminary experiments we had found that doses up to a rate of 5000 rad of x-rays were sufficient to keep protoplasts of *S. nigrum* from having more than 2 divisions per cell, before ceasing to divide. When fusions were performed with such dose rates, fusion products bearing both potato and *S. nigrum* morphological markers such as leaf hair shape were obtained. Thus, this dose rate was clearly insufficient and higher dose rates had to be used. For this reason, a dosage of 7000 rad was used which gave fusion products without any sign of *S. nigrum* morphological markers. An Andrex, Copenhagen, Denmark, model BW 434 X-ray machine giving 580 rad/min and uniform beam covering an area with a 3 cm diameter was used. The dose was given as a single continuous dose which lasted about 12.1 minutes. Because of variations in instrument geometry and calibration, anyone trained in the state of the art will calibrate his own system finding a dose giving viable fusants without donor morphological markers. Prior to irradiation, protoplasts were filtered through a Nitex, nylon monofilament screen (100 micron pore diameter) to remove debris, transferred to a sterile glass centrifuge tube with a screw top, and centrifuged for 1000×g for 5 minutes in a swinging bucket rotor. The enzyme medium was removed, and the protoplasts which remain on top of the medium were gently resuspended in the 3 ml CPW medium (Table 3) and placed in a 3 cm. diameter plastic tissue culture dish for irradiation.

Preparing protoplasts for fusion

The ionizing radiation of the donor can cause the formation of potentially toxic free radicals and their products. It is thus necessary to immediately wash the protoplasts as follows using medium (Table 3). The donor, protoplasts were rinsed 2 more times at 500×g for 5 minutes, with the protoplasts sedimenting to the bottom of the tube each time in CPW medium. The debris was removed from the recipients, and washed twice in CPW as outlined for the donors.

TABLE 3

| Modified CPW Medium (cf. Frearson et al 1973) | | |
|---|---|---|
| Component | mg/l | g/l |
| Mannitol | | 100 |
| $KH_2PO_4$ | | 0.027 |
| $CaCl_2.2H_2O$ | | 1.5 |
| $MgSO_4$ | | 0.246 |
| $KNO_3$ | | 0.101 |
| KI | 0.166 | |
| $CuSO_4$ | 0.025 | | adjusted to pH 5.8 with NaOH and autoclaved.

Protoplast fusion and washing

Donor and recipient protoplasts were mixed (after removing an aliquot for non-fused controls) in a ratio of two donor to one recipient and a final protoplast density of ca. 2 million per ml. 0.4 ml of the mixed protoplasts were mixed with 0.3 ml of a fusion inducing solution I, found optimal for this system containing: filter sterilized, 0.1 mM glucose, 40% w/v polyethylene glycol-MW 3350 (Sigma) and 55 mM Ca $(NO_3)_2$. The protoplasts were incubated for 15 minutes at room temperature. 3 ml of fusion inducing solution 2 containing 275 mM $Ca(NO_3)_2$ pH 10.5, were added and incubated for an additional 15 minutes. The material was transferred from the petri plates in which fusion was performed, diluted to about 7 ml with CPW (Table 3) centrifuged at 500×g for 5 minutes, and the pellets suspended in regeneration medium (Table 4) to make a solution containing $5 \times 10^4$ protoplasts. Three ml of the diluted protoplasts were each transferred to a 3 cm plastic tissue culture petri plate sealed with Parafilm (TM) and incubated for 20 hours at 5° C. Following the incubation the protoplasts, they were transferred to a growth room maintained at 24° C.

TABLE 4

| Protoplast regeneration medium | | | |
|---|---|---|---|
| Component | mg/l | component | mg/l |
| $Ca(NO_3)_2.4H_2O$ | 1000 | glutamine | 100 |
| $MgSO_4.7H_2$ | 500 | aspartic acid | 100 |
| $K_2PO_4$ | 230 | glucose | 5000 |
| $KNO_3$ | 1200 | sucrose | 10000 |
| KCl | 300 | mannitol | 73000 |
| $FeSO_4$ | 28 | 2,4,dichlorophenoxy acetic acid | 0.1 |
| $Na_2EDTA$ | 37 | naphthalene acetic acid | 1 |
| $H_3BO_4$ | 3 | zeatin (Trans isomers) | 0.5 |
| $MnSO_4.H_2O$ | 10 | | |
| $ZnSO_4.7H_2O$ | 2 | | |
| $Na_2MoO_4.2H_2O$ | 0.25 | pyridoxine HCl | 1 |
| $CuSO_4.5H_2O$ | 0.025 | nicotinic acid | 1 |
| $CaCl_2.6H_2O$ | 0.025 | Folic acid | 0.4 |
| KI | 0.75 | biotin | 0.01 |
| myo-inositol | 1000 | thiamine HCl | 10 |
| casein hydrolysate | 10 | fumaric acid | 40 |
| | | citric acid | 40 |
| Ca panthothenate | 1 | maleic acid | 40 |
| Choline-Chloride | 1 | pyruvic acid | 20 |
| P—aminobenzoic acid | 0.02 | | |
| | | coconut water(Gibco) | 20 ml/l |

The pH was adjusted to 5.6 with NaOH and the material was filter sterilized through a 0.22 micrometer Nalgene filter. This medium is a modification of Adams and Townsend (1983) and Michayluk (1975) Bokelmann (1983). Note: Ammonium ions in such medium were found to be toxic to the fusion products.

Callus regeneration from protoplasts

Protoplasts were kept in the growth room under 150 lux for one week (until after the first division) and then maintained at 1500 lux for an additional month. 10 days after the fusion, the osmoticum was lowered by adding to each dish, 1 ml of protoplast regeneration medium also containing 36 g/l mannitol. The osmoticum was again lowered 5 days later, by adding to each dish an additional 1 ml. of protoplast regeneration medium which also containing 36 g/l mannitol. A third and fourth lowering of osmoticum were done 5 and 7 days (respectively) using 1 ml protoplast regeneration medium (Table 4) each time except with no mannitol in the regeneration medium. By this time microcalli of about 3 mm in diameter were obtained. The microcalli were transferred to a 1% agar gelled medium for callus growth. This medium was M & S medium (Table 1) to which were added 1 mg/l naphthalene acetic acid and 0.1 mg/l zeatin (trans isomer). The micro-calli were incubated on this medium for about 6 weeks at 24° C., 1500 lux until the calli reached about 7 mm diameter.

Shoot regeneration from calli

The calli were transferred in the following medium which was found to be excellent for the regeneration of shoots from protoplast derived calli of potatos cv. Mirka. M & S medium (Table 1) to which 0.1 mg/l gibberellic acid, 0.2 mg/l abscissic acid, 10 mg/l zeatin (trans isomer) and 10 mg/l kinetin. Of all potato varieties used so far, only cv Mirka requires such a high level of cytokinins for shoot regeneration. These levels prevent shoot regeneration in all other varieties tested. These were incubated at 1500 lux at 24° C. Shoots began appearing two weeks later. When the shoots were 5 to 6 mm long, the small leaves were examined for signs of *S. nigrum* type leaf hairs, using a binocular microscope. (cf Binding et al (1982) for a description and picture). None had any resemblance to *S. nigrum*. The shoots were excised at this length and transferred to M & S medium (Table 1) containing only 1% sucrose and 0.8% agar and to which 0.1 mg/l gibberellic acid and 1 mg/l zeatin were added. This medium allowed more rapid growth. After about 3 weeks of growth on this medium they were transferred to the standard potato explant medium M & S (Table 1) except with 1% sucrose, and denoted "primary fusant explants". All treatments were in 6000 lux, 24° C.

Selection of resistant segregants

The chloroplast genomes of potatoes and *S. nigrum* usually segregate in fusion to produce cells which contain either one or the other genome after a few divisions. We tested secondary explants from each primary fusant explant on M & S medium (Table 1) containing only 0.35% sucrose and 100 micro molar reagent grade atrazine purchased from Riedel de Haen A. G., Hannover, W. Germany. The atrazine was made up fresh as a 10 mM solution in methanol and was dispersed in the cooling 0.8% agar medium before it gelled. The explants were inserted in the agar through a sheet of black filter paper (Eaton Dikeman 8613) and observed and compared with parental explants of potato cv. Mirka as controls during incubation at 24° C. at 6000–7000 lux. The black filter paper was used to prevent direct illumination of the agar.

About two thirds of the fusant explants and all of the controls became severely chlorotic within 7-10 days. Both the chlorotic offspring and these primary fusant explant lines were discarded. If all explants from a given calli-clone were chlorotic, the callus too was discarded. The deep green explants not affected by atrazine were returned to fresh explant medium and allowed to continue growing for further propagation and rechecking on atrazine medium. As atrazine is slowly photodegraded to metabolites that are potentially toxic at the concentration used, the test cannot be continued indefinetly. In soil culture, photodegradation of atrazine is not a problem.

Stem explants of calli-clonal lines of S. tuberosum c.v. Mirka Tri-R C-165 (atrazine resistant) have been deposited as meristem shoots with the American Type Culture Collection as a culture deposit under accession number ATCC 40164. This deposit was made pursuant to the Budapest Treaty On The International Recognition Of The Deposit of Microorganisms For The Purposes of Patent Procedure.

Rooting of resistant explants

Potato explants growing in the M & S medium (Table 1) but with 0.8% agar and 1% sucrose normally form roots within a week, and after a few weeks have a sufficient root system for transferring to a growth medium for ultimate potting.

Transfer to pots

Rooted explants were removed from the agar, excess agar washed off with sterile distilled water and transferred to pre-autoclaved "Jiffy Pots" (Jiffy Products Ltd. Norway) which were saturated with water, inside a sterile container.

After a few weeks growth in the growth room at 6000 lux, the covers were removed and the plants first placed in a high humidity chamber, for two days. The plants were then transferred to a standard greenhouse, with the Jiffy pots placed whole into a standard potting soil.

EXAMPLE 2

Obtaining Triazine Resistance in S. tuberosum cv. Desiree

In this example, the maternally-inherited triazine resistance trait which evolved in the Solanum nigrum was transferred into the crop Solanum tuberosum cv. Desiree using the techniques detailed in Example 1 except for the following changes:

(a) Pretreatment of the recipient protoplasts.

After protoplast isolation and washing, but before fusion, the protoplasts were treated with 0.25 mM iodoacetate (Aldrich) in CPW medium (Table 3) for 30 minutes. This treatment inactivates the organelles of the recipient, giving a higher percentage of triazine resistant fusion regenerants.

(b) Shoot regeneration from calli.

MS medium (Table 1) was modified by adding 0.1 mg/l gibberellic acid, 0.01 mg/l Naphthalene acetic acid, 2 mg/l zeatin (trans-isomer) and 1 mg/l zeatin-riboside. This regeneration medium does not work for cv. Mirka, but is excellent for Desiree and many other cultivars.

(c) Selection of resistant segregants.

Stems from in vitro cultured shoots with 4-5 nodes were put in 250ml Erlenmeyer flasks with 20 ml of MS liquid medium (Table 1) containing only 0.3% sucrose and 10 micro molar reagent grade atrazine and were shaken at 70 RPM at 25° C. at 7000 lux. No black filter paper was used under these conditions. The deep green explants not affected by atrazine after 25-30 days of growth were returned to fresh MS agar medium for rooting.

Rooted explants were removed from the agar and transferred to "Jiffy Pot s" and grown in the growth room at 6000 lux for two days. The plants were then transferred to a standard greenhouse and were tested for field resistance using commercial grade atrazine at a 1 kg/ha rate equivalent to applied to the soil.

Stem explants of calli-clonal lines of S. tuberosum cv. Desiree Tri-R (atrazine resistant) have been deposited as axenic stem explants with the American Type Culture Collection as a Culture Deposit For Patent Purposes under Accession Number 40224.

REFERENCES

Adams, T. L. and Townsend, S. A. (1983) A new procedure for increasing efficiency of protoplast relating and clone selection. *Plant Cell Report*, 2: 165–168.

Binding, H., Jain, S. M., Finger, J., Mordhorst, G., Nehls, R., and Gressel, J., (1982) Somatic hybridization of an atrazine resistant biotype of *Solanum nigrum* with *S. tuberosum*; I Clonal variation in morphology and in atrazine sensitivity. *Theor. Appl. Genet*, 63: 273–277.

Bokelmann, G. S. and Roset, S. (1983) Plant regeneration from protoplast of potato (*Solanum tuberosum* c.v. Bintje). *Z. Pflanzenphysiol. Bd.*, 109: 259–265.

Frearson, E. N., Power, J. B. and Cooking, E. C. (1973) The isolation, culture and regeneration of Petunia leaf protoplasts. *Developmental Biology*, 33, 130–137.

Gressel, J. (1985) Biotechnologically conferring herbicide resistance in crops: The present realities. in: *Molecular Form and Function of the Plant Genome*. L. Van Vloten-Doting, ed. Plenum, N.Y. (in press).

Gressel, J., Ezra, G. and Jain, S. M. (1982) Genetic and chemical manipulation of crops to confer tolerance to chemicals. In: J. S. McLaren, ed., *Chemical Manipulation of Crop Growth and Development*, Butterworths, London, pp. 79–91.

Gressel, J., Cohen, N. and Binding, H. (1984) Somatic hybridization of an atrazine resistant biotype of *Solanum nigrum* with *Solanum tuberosum*. II: Segregation of plastomes. *Theor. Appl. Genet.* 67: 131–134.

Gressel, J., Zilkah, S. and Esra, G. (1978) Herbicide action, resistance and screening in cultures vs. plants. In: "*Frontiers of Plant Tissue Culture 1978*", T. A. Thorpe, ed., University of Calgary Press, pp. 427–436.

Kao, K. M. and Michayluk, M. R. (1975) Nutritional requirements for growth of *Vicia bajastana* cells and protoplasts at very low population density in liquid media, *Plant* 126, 105–110.

Murashige, T. and Skoog, F. (1962) A revised medium for rapid growth and bio assays with tobacco time cultures, *Physiol. Plant* 15, 473–497.

Nagy, J. I. and Maliga, P. (1976) Callus induction and plant regeneration from mesophyll protoplasts of *Nicotiana sylvestris. Z. Planzenphysiol* 78. 453–455.

Souza-Machado, V Inheritance and breeding potential of triazine tolerance and resistance in plants. In:

*Herbicide Resistance in Plants,* (H. LeBaron and J. Gressel eds). J. Wiley, 1982. pp. 257-273.

Zelcer, A., Aviv, D. and Galun, E. (1978) Interspecific transfer of cytoplasmic male sterility by fusion between protoplasts of normal *Nicotiana sylvestris* and X-ray irradiated protoplasts of male-sterile *N. tabacum, Z. Pflanzenphysiol.,* 90: 397-407.

What is claimed is:

1. A method of producing triazine-resistant *Solanum tuberosum* cv. Mirka plants which comprises:
   (a) vegetatively propagating calli or *Solanum tuberosum* cv. Mirka Tri-R C-165 (ATCC Accession No. 40164) in a first growth medium comprising the modified Murashige and Skoog basal medium of Table 1 to which has been added about 0.1 mg/l gibberellic acid, about 0.2 mg/l abscissic acid, about 10 mg/l zeatin (trans-isomer) and about 10 mg/l kinetin under suitable conditions to generate plantlets having shoots and roots; and
   (b) transferring the plantlets having a sufficient root system to a suitable second growth medium, wherein the rooted plantlets are propagated under suitable conditions to produce mature triazine-resistant *Solanum tuberosum* cv. Mirka plants.

2. The method of claim 1, wherein the suitable conditions for generating roots comprise transferring the shoots to a suitable medium which induces rooting.

3. The method of claim 1, wherein the first growth medium is an agar or agarose nutrient medium.

4. The method of claim 1, wherein the conditions for generating shoots comprise light and a temperature of about 24° C.

5. The method of claim 1, wherein the second growth medium is soil.

6. A method of producing triazine-resistant *Solanum tuberosum* cv. Desiree plants which comprises:
   (a) vegetative propagating calli of *Solanum tuberosum* cv. Desiree Tri-R (ATCC Accession No. 40224) a first growth medium comprising the modified Murashige and Skoog basal medium of Table 1 to which has been added about 0.1 mg/l gibberellic acid, about 0.1 mg/l naphthalene acetic acid, about 2 mg/l zeatin (trans-isomer) and about 1 mg/l zeatin-riboside under suitable conditions to generate plantlets having shoots and roots; and
   (b) transferring the plantlets having a sufficient root system to a suitable second growth medium, wherein the rooted plantlets are propagated under suitable conditions to produce mature triazine-resistant *Solanum tuberosum* cv. Desiree plants.

7. The method of claim 6, wherein the suitable conditions for generating roots comprise transferring the shoots to a suitable medium which induces rooting.

8. The method of claim 6, wherein the first growth medium is an agar or agarose nutrient medium.

9. The method of claim 6, wherein the conditions for generating shoots comprise light and a temperature of about 24° C.

10. The method of claim 6, wherein the second growth medium is soil.

* * * * *